United States Patent [19]

Mehtali et al.

[11] Patent Number: 5,981,258
[45] Date of Patent: Nov. 9, 1999

[54] COMPOSITION OF TRANS-DOMINANT VARIANTS OF VIRAL PROTEINS FOR OBTAINING AN ANTIVIRAL EFFECT

[75] Inventors: Majid Mehtali, Illkirch-Graffenstaden; Tania Guss, Dossenheim-sur-Zinsel, both of France

[73] Assignee: Transgene S.A., Strasbourg, France

[21] Appl. No.: 08/505,210

[22] PCT Filed: Dec. 13, 1994

[86] PCT No.: PCT/FR94/01457

§ 371 Date: Aug. 14, 1995

§ 102(e) Date: Aug. 14, 1995

[87] PCT Pub. No.: WO95/16780

PCT Pub. Date: Jun. 22, 1995

Related U.S. Application Data

[63] Continuation-in-part of application No. 08/215,248, Mar. 21, 1994, abandoned.

[30] Foreign Application Priority Data

Dec. 13, 1993 [FR] France ................................ 93 14914

[51] Int. Cl.⁶ ...................... A61K 39/21; C07K 14/155; C12N 5/10
[52] U.S. Cl. ...................... 435/235.1; 435/320.1; 435/69.3; 435/372; 424/208.1; 424/188.1; 530/350; 536/23.72
[58] Field of Search ............................ 435/235.1, 320.1, 435/69.3, 372; 424/208.1, 188.1; 530/350; 536/23.72

[56] References Cited

FOREIGN PATENT DOCUMENTS 0 406 557   1/1991   European Pat. Off. .

OTHER PUBLICATIONS

Haynes et al. Ann. Med., Trends in Molecular Medicine, vol. 28, pp. 39–41, 1996.
Plavec et al. Gene Therapy, vol. 4, pp. 128–139, 1997.
Fox "No Winner against AIDS" Bio/Technology vol. 12, Feb. 1994, p. 128.
Feinberg et al. "Intracellular Immunization: Trans–dominant Mutants . . . " AIDS Res. and Human Retroviruses vol. 8, No. 6, 1992, pp. 1013–1022.
Liem et al. "The Development and Testing of Retroviral Vectors . . . " Human Gene Therapy, vol. 4, No. 5, Oct. 1993, pp. 625–634.
Rosen "Tat and Rev: positive modulators of human . . . " Gene Expression vol. 1, No. 2, May 1991, pp. 85–90.
Pearson et al, "A transdominant tat mutant that inhibits . . . " PNAS, USA vol. 87, No. 13, Jul. 1990, pp. 5079–5083.
Bevec et al. "Inhibition of human immunodeficiency virus . . . " PNAS, USA vol. 89, No. 20, 1992, pp. 9870–9874.
Journal of Virology, vol. 67, No. 6, Jun. 1993, pp. 3199–3207, Bahner et al, "Comparison of Trans–Dominant Inhibitory Mutant Human Immunodeficiency Virus Type 1 Genes Expressed by Retroviral Vectors in Human T Lymphocytes".
J. Lisziewicz et al., "Efficacy of antitat Gene Therapy in the Presence of High Multiplicity Infection and Inflammatory Cytokines," Human Gene Therapy, 7:2209–2216, Dec. 1, 1996.
M. Bonyhadi et al., "RevM10—Expressing T Cells Derived in Vivo from Transduced Human Hematopoietic . . .", Journal of Virology, vol. 71, No. 6, pp. 4707–4716, Jun. 1997.
U. Ranga et al., "Enhanced T cell engraftment after retroviral delivery of an antiviral gene in HIV–infected individuals," Proc. Natl. Acad. Sci. USA, vol. 95, pp. 1201–1206, Feb. 1998.
M.C. Poznansky, "Inhibition of human immunodeficiency virus replication . . .", Human Gene Therapy, 9:487–496, Mar. 1998.
Ulich et al., "Inhibition of human immunodeficiency virus type 1 replication is enhanced . . .," J. Virol, 70(7):4871–4876, Jul. 1996 (Abstract).
Akkina et al., "Modeling Human Lymphoid Precursor Cell Gene Therapy in the SCID–hu Mouse," Blood, 84(5):1393–1398 (1994).
Cournoyer, "Gene Therapy Of The Immune System," Annu Rev. Immunol., 11:297–329 (1993).
Gilboa et al., "Gene therapy for infectious diseases: the AIDS model," Trends in Genetics, 10(4) 139–144.
Green et al., "Mutational Analysis of HIV–1 Tat Minimal Domain Peptides: Identification of Trans–Dominant Mutants That Suppress HIV–LTR–Driven Gene Expression," Cell 58:215–223 (1989).
Haynes, "Scientific and Social Issues of Human Immunodeficiency Virus Vaccine Development," Science, 260:1279–1286 (1993).
Johnston et al., "Present Status and Future Prospects for HIV Therapies," Science 260:1286–1293 (1993).
Ledley, "Clinical Considerations in the Design of Protocols for Somatic Gene Therapy," Human Gene Therapy, 2:77–83 (1991).
Mitsuya et al., "Strategies for antiviral therapy in AIDS," Nature, 325:773–778 (1987).
Orkin et al., "Report and Recommendations of the Panel to Assess the NIH Investment in Research on Gene Therapy," Dec. 7, 1995.

(List continued on next page.)

Primary Examiner—Ponnathapura Achutamurthy
Assistant Examiner—Phuong T. Bui
Attorney, Agent, or Firm—Burns, Doane, Swecker & Mathis, L.L.P.

[57] ABSTRACT

A composition resulting from a combination of trans-dominant variants of two viral proteins from a single virus, and the use thereof as a combination product are disclosed. A vector for expressing the two variants, a eukaryotic cell containing same, and a pharmaceutical composition for treating viral infections, are also disclosed.

10 Claims, 8 Drawing Sheets

OTHER PUBLICATIONS

Rice et al., "Mutational Analysis of the Conserved Cysteine–Rich Region of the Human Immunodeficiency Virus Type 1 Tat Protein," *Journal of Virology*, 64(4):1864–1868 (1990).

Venkatesh et al., "Mutants in a Conserved Region near the Carboxy–Terminus of HIV–1 Rev Identify Functionally Important Residues and Exhibit a Dominant Negative Phenotype," *Virology*, 178:327–330 (1990).

Woffendin et al., "Expression of a protective gene prolongs survival of T cells in human immunodeficiency virus–infected patients," *Proc. Nat'l. Acad. Sci. USA*, 93:2889–2894 (1996).

COMPOSITION OF TRANS-DOMINANT VARIANTS OF VIRAL PROTEINS FOR OBTAINING AN ANTIVIRAL EFFECT

This application is a 371 of PCT/FR94/01457 and a continuation-in-part of U.S. Ser. No. 08/215,248, filed Mar. 21, 1994, now abandoned.

The present invention relates to a composition resulting from the combination of trans-dominant variants of two viral proteins originating from the same virus. The combination of these two variants enables a resistance to infection by or propagation of the virus in question to be conferred. The present invention finds an advantageous application in the treatment or prevention of infections caused by HIV (human immunodeficiency virus) responsible for AIDS (acquired immunodeficiency syndrome).

In the context of the search for and preparation of medicinal products that inhibit viral infections, somatic gene therapy by intracellular immunization constitutes one of the promising approaches for the future. This concept, defined by Baltimore (1988, Nature, 335, 395–396), consists in genetically modifying cells so as to cause them to synthesize a nucleic acid or a heterologous protein endowing them with resistance against the viral infection. One of the possible approaches for acquiring this resistance is to cause the host cell to synthesize genes that inhibit a step of the viral cycle. Although all the steps of the viral cycle may be targeted in order to implement such a therapy, the genes participating in an early step constitute a potentially advantageous target. Such is the case with the tat and rev genes of the HIV virus, which play an essential part in initiation of the viral replication.

The tat gene codes for a TAT protein which transactivates the expression of all of the genes of HIV (Arya et al., 1985, Science, 229, 69–73). It appears that TAT participates at both transcriptional and post-transcriptional level. It interacts specifically with a short nucleotide sequence localized at the 5' end of the genome and of the viral transcripts and designated TAR (standing for trans-activation responsive region) sequence (Rosen et al., 1985, Cell, 41, 813–823).

The REV protein, the expression product of the rev gene, promotes the transport of large-sized messenger RNA (mRNA) to the cytoplasm, to be translated therein. For its part, REV specifically recognizes an RRE (standing for REV responsive element) sequence on the mRNA. This sequence is localized in proximity to another sequence termed CRS (cis-acting repression sequence), involved in the nuclear retention of the mRNA carrying it. It is assumed that binding of the REV protein to its RRE target sequence has the effect of counterbalancing the inhibitory effect of CRS on the passage of large viral mRNA into the cytoplasm.

Although their expression products are very different from a molecular mass, sequence and mechanism of action standpoint, regulator genes exerting a function similar to TAT and/or REV have been identified in the genome of other infectious viruses, such as HTLV-I and -II (human T-cell leukemia virus) retroviruses responsible for severe forms of leukemia and herpesviruses (chicken pox, shingles and Epstein-Barr viruses).

For some years, negative and dominant (transdominant) mutants of these various viral proteins have been described in the literature. In particular, several teams have generated trans-dominant variants of the TAT and REV proteins capable of binding to their target sequence but incapable of exerting the function of the native protein. While their inhibitory effect with respect to the action of the native protein has been demonstrated, their efficacy in HIV-infected cells nevertheless remains to be determined.

It has now been found that the expression in an HIV-infected cell of at least two genes coding for transdominant variants of the TAT and REV proteins, respectively, of the HIV virus enables propagation of the virus to be blocked. The authors have demonstrated that the inhibition of viral infection resulting from the joint expression of the two genes is markedly greater than that observed on expression of either one of these genes. This synergistic effect constitutes an unexpected advantage.

The objective of the present invention is to make available to the public an especially effective pharmaceutical composition, and which is hence safer for the purpose of use in humans, which enables the replication of a virus to be inhibited at different points of the viral cycle.

Thus, the subject of the present invention is a composition comprising at least:

(a) a first trans-dominant variant of a viral protein; and
(b) a second trans-dominant variant of another viral protein originating from the same virus as the viral protein in (a).

In the context of the invention, a first and a second trans-dominant variant are preferably derived from proteins originating from the viruses HTLV-I and -II (human T-cell leukemia virus), HSV-1 (herpes simplex virus) and as an absolute preference, HIV. Under the name "HIV" are grouped together the different viral strains and isolates of the virus which is the etiological agent of AIDS.

"Trans-dominant mutant" is understood to mean a negative and dominant mutant, that is to say a mutant which is non-functional (incapable of exerting the function of the native protein from which it is derived) but capable of competitively and dominantly inhibiting the function of the latter. In practice, a trans-dominant variant can be obtained by deletion, substitution and/or addition of one or more amino acids of the native protein or of a functional fragment of the latter. A person skilled in the art knows the techniques which enable these modifications to be performed, as well as the regions which have to be modified according to the viral proteins under consideration.

However, and according to an advantageous embodiment, the first and the second trans-dominant variants employed in the context of the present invention are derived from viral proteins participating in an early stage of the infection, and in particular from proteins capable of interacting specifically with a particular nucleotide sequence (termed target sequence) present in the genome and/or the transcripts of the virus from which they originate.

It is preferable to employ a first trans-dominant variant derived from a protein exerting a trans-activating function, in particular from the VP16 protein of HSV-1 (Friedman et al., 1988, Nature, 335, 452–454), the p40 and p37 proteins encoded by the X region of the genome of the HTLV-I and -II viruses (Wachsman et al., 1987, Science, 235, 674–677) and, as an absolute preference, the TAT protein of HIV (see below). As a second trans-dominant variant, a variant derived from a viral protein participating in another step, preferably early, of the viral replication, for example at the level of transport of the viral mRNA to the cytoplasm of the host cell, will be employed.

A preferred composition according to the invention results from the combination of:

(a) a first trans-dominant variant derived from the TAT protein of the HIV virus; and
(b) a second trans-dominant variant derived from the REV protein of the HIV virus.

The choice of a trans-dominant variant of the TAT protein is very wide. It can fall on those described in the prior art, and in particular in Green et al. (1989, Cell, 58, 215–233) and Pearson et al. (1990, Proc. Natl. Acad. Sci. USA, 87, 5079–5083). But it can also fall on other trans-dominant variants, in particular a variant having the sequence as shown in sequence identifier NO: 1, beginning at amino acid +1 and ending at amino acid +86, in which:

(1) the phenylalanine residue at position +38 is replaced by an aspartic acid residue;

(2) the threonine residue at position +40 is replaced by an alanine residue;

(3) the lysine residue at position +41 is replaced by a glutamic acid residue;

(4) the isoleucine residue at position +45 is replaced by a serine residue; and/or (5) the tyrosine residue at position +47 is replaced by an arginine residue.

Naturally, a trans-dominant TAT variant can combine several mutations.

As examples of trans-dominant variants of the REV protein, there may be quoted those mentioned in Malim et al. (1989, Cell, 58, 205–214) and Venkatesh and Chinnadurai (1990, Virology, 178, 327–330). However, it can be advantageous to employ other trans-dominant variants, such as a variant having the sequence as shown in sequence identifier NO: 2, beginning at amino acid +1 and ending at amino acid +116, in which the glutamine (Gln) residue at position +74 is replaced by a glycine (Gly) residue, and the leucine (Leu) residue at position +75 is replaced by a serine (Ser) residue; hereinafter designated REV (Gln$^{74}$, Leu$^{75}$→ Gly, Ser). Moreover, the use of variants modified in respect of three amino acids and more, especially in respect of the Leu residues at positions 75, 78 and 81, can prove advantageous. To illustrate this embodiment, there may be mentioned an REV variant mutated at 5 positions, in which variant the codons encoding the residues Gln$^{74}$, Leu$^{75}$, Leu$^{78}$, Glu$^{79}$ and Leu$^{81}$ have been replaced by codons encoding the residues Gly, Ser, Glu, Phe and Asp respectively.

The present invention also relates to a composition according to the invention, as a combination product for use simultaneously, separately or spread over time, for the treatment or prevention of infections caused by the virus from which the viral proteins in question originate. The use of such a composition is intended more especially for AIDS therapy.

In accordance with the objectives pursued by the present invention, a first and a second trans-dominant variant may be produced by recombination methods, in a composition according to the invention, from suitable expression vectors. Use will advantageously be made of viral vectors derived from retroviruses, adenovirus or adeno-associated virus, into which at least one DNA sequence coding for a trans-dominant variant in use in the present invention is inserted. The genome of these viral vectors is preferably defective for replication. It should be noted that, in the context of the present invention, retroviral vectors, and in particular those derived from MoMuLV (Moloney murine leukemia virus) are especially preferred. Such vectors as well as the techniques for preparing them are known to a person skilled in the art.

The DNA sequences coding for a trans-dominant variant of a viral protein may be obtained according to standard techniques of molecular biology. One of the possible strategies consists in first isolating the sequence coding for said viral protein from the viral genome, by cloning or PCR (polymerase chain reaction), and then in modifying it by directed mutagenesis to generate a desired trans-dominant variant. Alternatively, the DNA sequence of interest may be produced by chemical synthesis.

Naturally, the DNA sequences coding, respectively, for a first and a second trans-dominant variant in use in the present invention may be inserted into the same recombinant vector or into two different vectors. Furthermore, these vectors may contain a selectable gene facilitating isolation of the clones transfected by said vectors.

The present invention also relates to a recombinant vector capable of transferring and expressing:

(a) a first DNA sequence coding for a first trans-dominant variant of a viral protein; and (b) a second DNA sequence coding for a second trans-dominant variant of another viral protein originating from the same virus as the protein in (a).

According to an especially preferred embodiment, said first DNA sequence codes for a trans-dominant variant of the TAT protein of the HIV virus, and the second DNA sequence coding for a trans-dominant variant of the REV protein of the HIV virus.

Naturally, the first and second DNA sequences are placed under the control of the elements needed for their expression. These elements comprise, in particular, the regulatory elements for transcription of a DNA sequence to mRNA, as well as the initiation and termination signals for translation of the mRNA to protein. Among these elements, the promoter region assumes special importance.

Generally speaking, a promoter region which is functional in the eukaryotic cells which it is desired to treat, and preferably in human cells, is employed. A promoter region can originate from eukaryotic or viral genes, and can be constitutive or regulable, in particular in response to certain tissue-specific, and especially lymphocyte-specific, cellular signals. As examples, it is possible to envisage employing the promoter regions of the SV40 (simian virus 40) virus, of the PGK (phosphoglycerate kinase) gene, the HMG (hydroxymethylglutarylcoenzyme A) gene or the TK (thymidine kinase) gene of HSV-1, the LTRs (long terminal repeats) of RSV (Rous sarcoma virus), of MoMuLV and of HIV and the promoters of the E1A and E3 genes and MLP (major late promoter) of adenovirus. It should be noted that these examples are not limiting.

The present invention encompasses eukaryotic cells into the genome of which a first and a second sequence employed in the context of the invention are inserted. The vector or vectors carrying said sequences may be introduced either in vitro into a cell removed from the patient, or directly in vivo. Preferably, said cell is a human cell and, as an absolute preference, a stem cell of the hematopoietic line or a lymphocyte.

The invention is also directed towards the use of a composition, a vector or a celinaccording to the invention for the preparation of a medicinal product intended for the treatment of viral infections by gene therapy, and in particular infections caused by HIV.

The invention also relates to a pharmaceutical composition, which comprises as therapeutic or prophylactic agent a composition, a vector or a cell according to the invention, in combination with a vehicle which is acceptable from a pharmaceutical standpoint.

Such a pharmaceutical composition according to the invention may be prepared according to techniques in common use, and administered according to any known administration route. For example, a therapeutically effective amount of the therapeutic or prophylactic agent is combined with an acceptable vehicle, diluent or adjuvant. The amount to be administered will be chosen in accordance with various criteria, especially the administration route, the pathology in question, the first and second DNA sequences to be expressed or the patient and the desired duration of treatment.

Moreover, the invention relates to a kit containing:
(a) a first trans-dominant variant of a viral protein, and
(b) a second trans-dominant variant of another viral protein originating from the same virus as the viral protein in (a);

with directions for their concomitant or sequential administration.

Lastly, the invention relates to a method of treatment of viral infections, and most especially those caused by HIV, according to which a therapeutically effective amount of a composition, a vector or a cell according to the invention is administered to a patient requiring such a treatment.

As a guide, the essential steps for an antiviral treatment by gene therapy are as follows:
a bone marrow or blood sample is taken from a patient requiring such a treatment;
the cells removed (stem cells or lymphocytes) are cultured according to the techniques used in the art;
a vector according to the invention into which the sequences coding for a first and a second transdominant variant is transfected. However, it is also possible to cotransfect, or alternatively to transfect separately and over a period of time, each of the vectors permitting the expression of one or other of the trans-dominant variants. An additional step of culture in a selective medium is performed where appropriate; and
the cells thus modified are reinjected into the patient.

Naturally, the details of this therapeutic protocol may be subject to many variants determined by clinicians.

BRIEF DESCRIPTION OF THE DRAWINGS

The invention is illustrated below by reference to the figures which follow.

EXAMPLES

Figure 1:
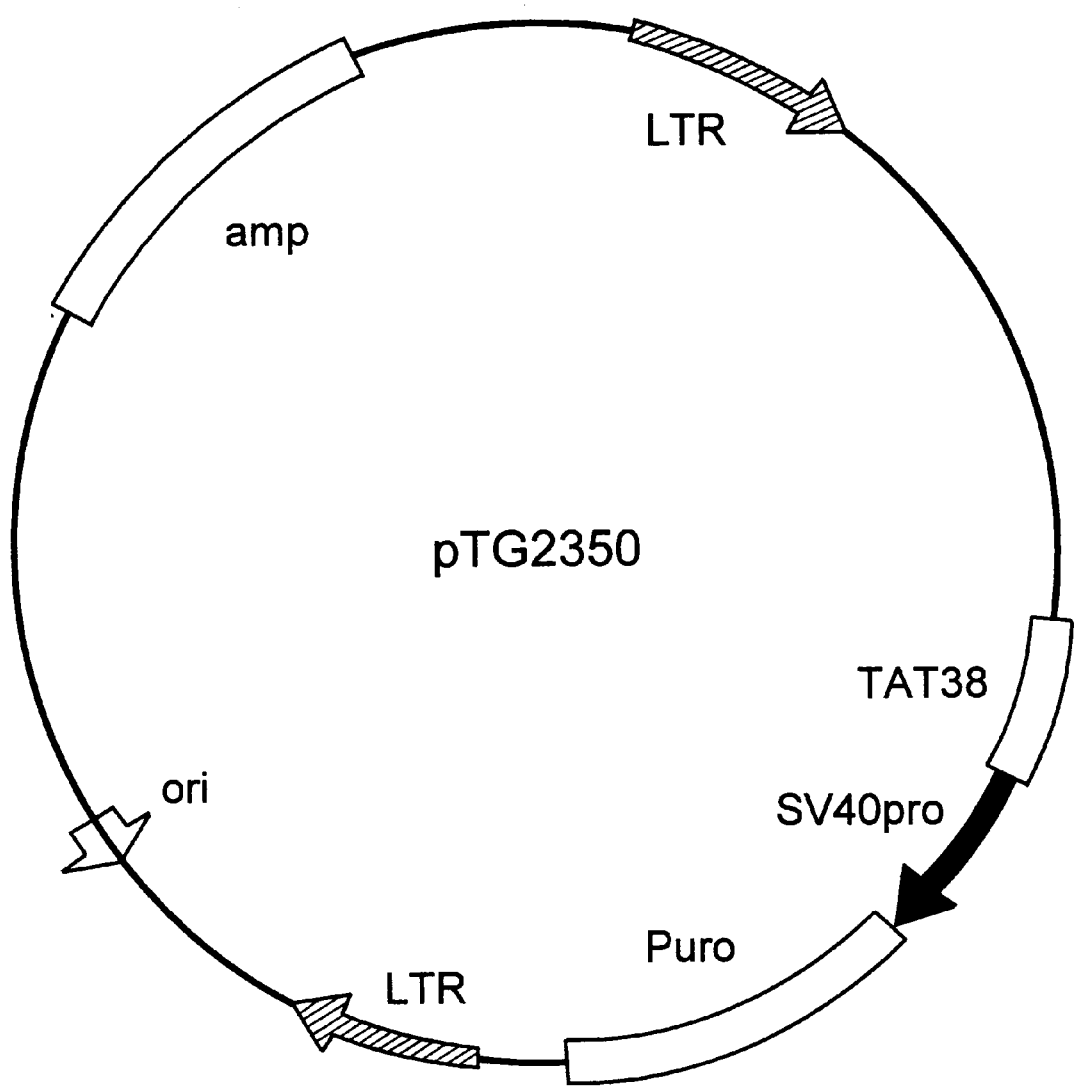
FIG. 1 shows diagrammatically the vector pTG2350 permitting the expression of a trans-dominant TAT (Phe$^{38}$→Asp) variant of HIV (TAT38), under the control of the retroviral 5' LTR.

The constructions described below are carried out according to the general techniques of genetic engineering and molecular cloning detailed in Maniatis et al. (1989, Laboratory Manual, Cold Spring Harbor Laboratory Press, Cold Spring Harbor, N.Y.). The set of cloning steps employing bacterial plasmids is performed by transfer in *Escherichia coli* (*E. coli*) strain 1106, BJ5183 or XL1-Blue, whereas those employing vectors derived from phage M13 are carried out in *E. coli* NM522.

As regards mutageneses directed by synthetic oligodeoxynucleotides, the protocol described by Zoller and Smith (1982, Nucleic Acids Res., 10, 6487) is applied, or a kit of commercial origin is employed according to the manufacturer's recommendations. As regards the repair of the restriction sites, the filling of the protruding ends may be performed by means of the Klenow fragment of DNA polymerase of *E. coli* and the destruction of the protruding 3' ends in the presence of T4 phage DNA polymerase or by treating with S1 nuclease followed by repair using Klenow. The PCR techniques are known to persons skilled in the art and are abundantly described in PCR protocols, a guide to methods and applications (Ed: Innis, Gelfand, Sninsky and White, Academic Press Inc.).

Moreover, the sequence of a trans-dominant TAT or REV variant is aligned with that of the TAT or REV protein of the HIV-1 virus, Lai isolate, as disclosed by Wain-Hobson et al. (1985, Cell, 40, 9–17). In practice, the numbering of the amino acids in the sequence of a trans-dominant variant will be modeled on that established for the native protein, the sequence as shown in sequence identifiers NO: 1 for the TAT protein and NO: 2 for the REV protein.

Furthermore, cell lines are cultured according to the supplier's recommendations. Generally speaking, cells are transfected according to the calcium phosphate technique (Maniatis et al., Molecular cloning: a laboratory manual, 1989, Cold Spring Harbor Laboratory), except for CEM-A3 cells for which electroporation is used. However, other protocols enabling a nucleic acid to be introduced into a cell may also be employed. Before any transfection, the DNA is purified on a cesium chloride gradient.

EXAMPLE 1

Establishment of a Cell Line Coexpressing the Trans-Dominant TAT and REV Variants.

A. Construction of the retroviral vector pTG2350 for expression of the trans-dominant TAT (Phe$^{38}$→Asp) variant and characterization of its trans-dominant phenotype.

A DNA fragment containing the copy DNA (cDNA) corresponding to the 2 exons of the tat gene of the HIV-Lai isolate genome (Wain-Hobson et al., 1985, Cell, 40, 9–17; Sodroski et al., 1985, Science, 229, 74–77) is modified in order to create a BamHI site at the 5' end of the initiation ATG. In addition, a BamHI site exists naturally at the 3' end of the stop codon. The 300-bp BamHI fragment containing the unmutated tat cDNA is inserted into the vector M13TG130 (Kieny et al., 1983, Gene, 26, 91–99). The vector M13TG2306 is obtained.

A trans-dominant TAT variant is generated by replacing the phenylalanine (Phe) residue at position 38 of the native TAT protein by an aspartic acid (Asp). M13TG2306 is subjected to a directed mutagenesis using a commercial kit (Amersham, RPN 1523) and employing the oligonucleotide described in sequence identifier SEQ ID NO: 3, giving M13TG2316.

The BamHI fragment isolated from the above vector is then transferred to the eukaryotic vector pSG5 (Green et al., 1988, Nucleic Acids Res., 16, 369). pTG2332, in which expression of the TAT (Phe$^{38}$→Asp) variant is under the control of the Sv40 promoter, is obtained.

The capacity of the TAT (Phe$^{38}$→Asp) variant to trans-activate the expression of the CAT (chloramphenicol acetyltransferase) gene placed under the control of the LTR of HIV including the TAR sequence (LTR-CAT; Emerman et al., 1987, EMBO, J., 6, 37–55) is evaluated. The trans-activating activity is determined by transient transfection into HeLa cells (ATCC CCL2) (4×10$^5$ cells per dish) of 1 μg of the expression vector pTG2332 with 0.5 μg of the reporter vector LTR-CAT. 1 μg of pHMG-Tat and 0.5 μg of LTR-CAT, which constitutes the positive control for trans-activation (100%) are transfected under the same conditions. pHMG-Tat is the vector for expression of the native TAT protein, and results from cloning of the BamHI fragment of M13TG2306 into the BamHI site of the vector pHMG (Mehtali et al., 1990, Gene, 91, 179–184).

48 h after the transfections, the level of expression of the CAT gene is measured on an aliquot of cell extract corresponding to 10 to 20 μg of protein according to the technique described in Gorman et al., (1982, Mol. Cell. Biol., 2, 1044–1051). The protein concentration is determined using a commercial kit following the protocol described by the supplier. The percentage trans-activating activity of the variant is calculated relative to the level measured with the positive control (pHMG-Tat+LTR-CAT), the latter representing 100% trans-activating activity.

The capacity of the TAT (Phe$^{38}$→Asp) variant to inhibit the trans-activating function of the native TAT protein is then determined by transient transfection into HeLa cells of the expression vector pTG2332 (10 μg) with the reporter vector LTR-CAT (0.5 μg) and the vector pHMG-Tat (1 μg). As above, the expression of the CAT reporter gene is measured on an aliquot of extract corresponding to 10 to 20 μg of protein. The percentage inhibition of the native TAT protein by the TAT (Phe$^{38}$→Asp) variant is calculated relative to the control resulting from the cotransfection of pHMG-Tat and LTR-CAT, which represents 0% inhibitory activity.

The TAT (Phe$^{38}$→Asp) variant is an effective trans-dominant mutant, since its trans-activating activity is reduced (expression of the CAT gene less than 10% relative to that measured with the native TAT protein) and since it strongly inhibits the activity of the native TAT protein (at least 90% inhibition).

The 300-bp BamHI fragment isolated from M13TG2316 is inserted into the BamHI site of the retroviral vector pLXSP, generating pTG2350 (FIG. 1). The vector pLXSP is derived from pLXSN (Miller and Rossman, 1989, Biotechniques, 7, 980–988) after replacement of the neomycin (neo) gene by a gene conferring resistance to puromycin and of the MSV (myelosarcoma virus) 3' LTR by the MPSV (myeloproliferative sarcoma virus) 3' LTR.

B. Construction of the retroviral vectors pTG2428 and pTG2430 for expression of the trans-dominant REV (Gln$^{74}$, Leu$^{75}$→Gly, Ser) variant and characterization of its trans-dominant phenotype.

An 830-bp SalI fragment comprising the copy DNA corresponding to the two coding exons of the rev gene of HIV-1-Lai isolate is inserted into the vector M13TG130, generating the vector M13TG2309. The latter is modified by directed mutagenesis (Amersham kit) in order to introduce two BglII sites flanking the sequence coding for REV, the first site upstream of the initiation ATG and the second downstream of the stop codon. The presence of these BglII sites enables the subsequent cloning steps to be facilitated. However, any other appropriate restriction site could have been chosen.

The vector thereby obtained is subjected to a directed mutagenesis employing the oligonucleotide OTG4672 reported in sequence identifier NO: 4, with the object of substituting the Gln and Leu residues at positions 74 and 75 of the native REV protein by Gly and Ser residues. The resulting vector is digested with BglII, and the 390-bp fragment is inserted into the eukaryotic expression vector pSG5 to give plasmid pTG REV.TD, on which the trans-dominant phenotype of the REV (Gln$^{74}$, Leu$^{75}$→Gly, Ser) mutant is evaluated.

Its activity with respect to the transport of mRNA is determined by transient transfection into the HeLa cell line of pTG REV.TD (1 μg) and the reporter vector pTG1335 (0.5 g). The latter comprises the CAT gene placed under the control of the SV40 promoter and the RRE/CRS elements of the HIV-1 genome inserted downstream of the CAT gene. Thus, in the absence of a functional REV protein, the CRS element will maintain the mRNA in the nucleus and no expression product of the CAT gene is detected. In contrast, in the presence of a functional REV protein, the latter will bind to its RRE target sequence and induce the transport of the mRNA to the cytoplasm and its translation.

Expression of the CAT gene is determined on an aliquot of cell extract under the same conditions as above. The percentage activity of the REV (Gln$^{74}$ Leu$^{75}$→Gly, Ser) mutant is calculated relative to the level measured with a positive control resulting from cotransfection of the vector pHMG-Rev permitting expression of the native REV protein and the reporter vector pTG1335, representing 100% REV activity.

In parallel, its capacity to inhibit the function of the native REV protein is evaluated by transient transfection of the expression vector pTG REV.TD (10 μg) and the reporter vector pTG1335 (0.5 μg) in the presence of 1 μg of the vector pHMG-Rev. The level of expression of the CAT gene is measured relative to the control resulting from the cotransfection of pHMG-Rev and pTG1335, and which represents 0% inhibition.

The REV (Gln$^{74}$, Leu$^{75}$→Gly, Ser) variant proves to be an effective trans-dominant variant which now has virtually no activity in the transport of mRNA to the cytoplasm, but which is capable of dominantly inhibiting the native REV function.

Figure 2:
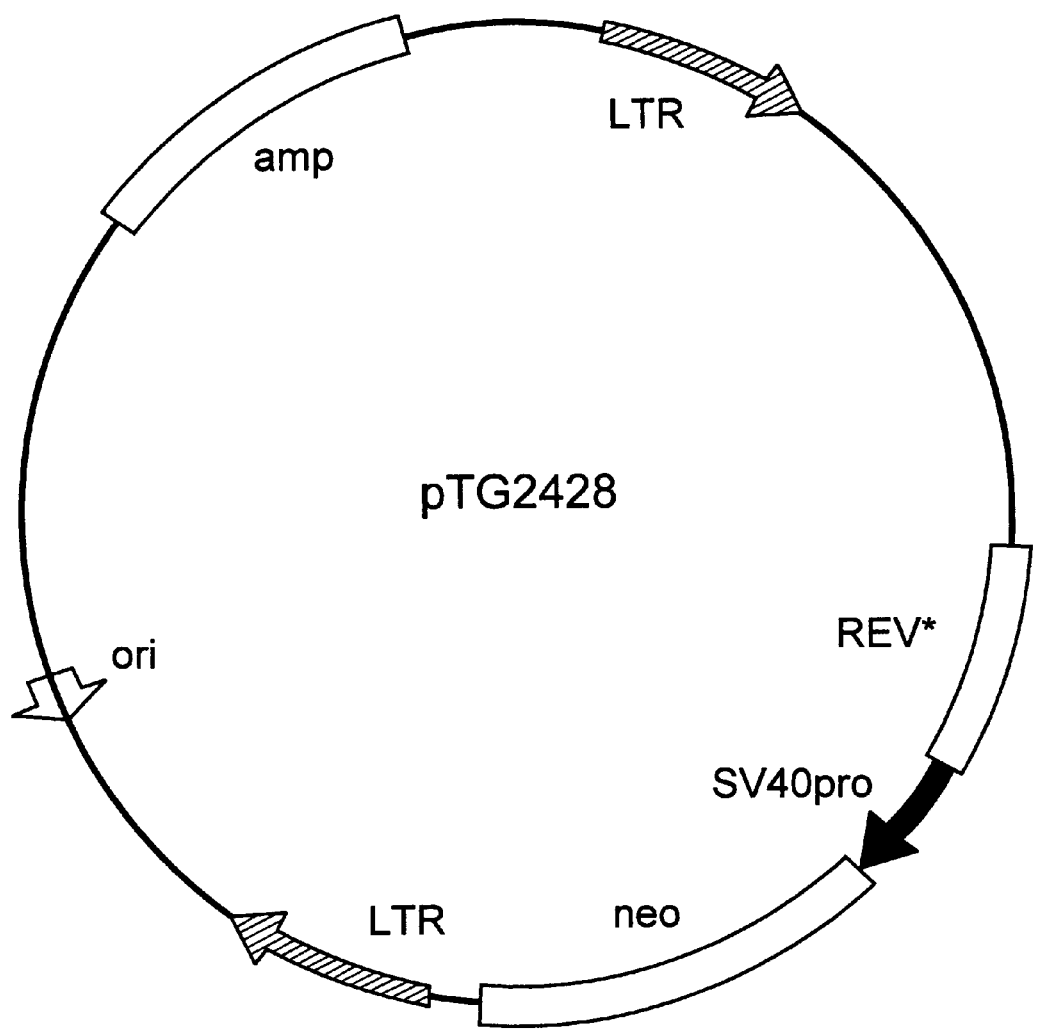
FIG. 2 illustrates the vector pTG2428 permitting the expression of the trans-dominant REV (Gln$^{74}$, Leu$^{75}$→Gly, Ser) (REV*) variant of HIV under the control of the retroviral 5' LTR.

The 390-bp BglII fragment carrying the coding sequence for the trans-dominant REV mutant is subcloned into the BamHI site of pTG5192. The latter is derived from pLXSN, in which the 3' LTR originating from MSV is replaced by the 3' LTR of MPSV. The retroviral vector pTG2428 (FIG. 2), also carrying the neomycin selectable marker which confers resistance to G418, is generated.

Moreover, the same BglII fragment is also inserted into the retroviral vector pLXSP to give pTG2430, carrying the puromycin resistance gene.

C. Establishment of a CEM-A3 cell line expressing the trans-dominant TAT (Phe$^{38}$→Asp) and REV (Gln$^{74}$, Leu$^{75}$→Gly, Ser) mutants.

A stable cell line coproducing both trans-dominant variants is established from cells which can be naturally infected with HIV, for example the CEM-A3 human lymphocyte line derived from CCRF-CEM (ATCC CCL119) and which strongly expresses the CD4 surface marker, and HIV receptor.

20 μg of pTG2350 plasmid DNA is electroporated into $2\times10^7$ CEM-A3 cells (Gene pulser Biorad, voltage 210V, capacitance 960 μF). The cells are then put up in culture again in RPMI medium (Gibco-BRL) at 37° C. in the presence of 5% of $CO_2$. Two days later, the cells are placed in a selective medium (0.5 μg/ml puromycin) and the resistant clones (CEM-A3 2350 cells) are isolated.

Expression of the trans-dominant variant in the different clones may be detected by transient transfection with the vectors LTR-CAT and pHMG-Tat and by measuring the extinction of the expression of the CAT gene relative to a control of cells of CEM-A3 origin transfected with these two vectors.

A puromycin-resistant clone is selected, into which 20 μg of pTG2428 are introduced according to the electroporation protocol mentioned above. The cells are placed in doubly selective medium (0.5 μg/ml puromycin and 1 mg/ml G418). The pool of cells resistant to both antibiotics is hereinafter designated CEM-A3 2350+2428.

By way of comparison, a CEM-A3 line producing the trans-dominant REV variant is also established, by transfection of the vector pTG2430. The puromycin-resistant cells are designated CEM-A3 2430.

EXAMPLE 2

Evaluation of the Resistance of CEM-A3 2350+ 2428 Cells to HIV Infection.

Approximately $10^6$ CEM-A3 2350+2428 cells are centrifuged at low speed. After washing, the cell pellet is taken up in 200 μl of RPMI medium in the absence of serum. The cells are infected with an HIV preparation at a $TCID_{50}$ of between 1 and 1000, and preferably 50 to 100. The $TCID_{50}$ is determined according to the method described in Reed et al. (1938, Am. J. Hyg. 27, 493–497) on cell lines which can be infected with HIV, such as, for example CEM-A3 cells, and corresponds to the dose at which 50% of the cells are infected and 50% are not. It is verified for each batch of HIV employed. Infection is continued for 1 h at 37° C.

The cells are then washed twice in RPMI and cultured in 5 ml of this same medium, supplemented with 10% of FCS (fetal calf serum). This step constitutes the T=0 of the experiment. The medium is renewed 2 or 3 times per week. Propagation of the virus is evaluated by measuring the reverse transcriptase activity at regular intervals in the culture supernatant according to the method described by Spire et al. (1985, Lancet i, 188–189).

Figure 3:
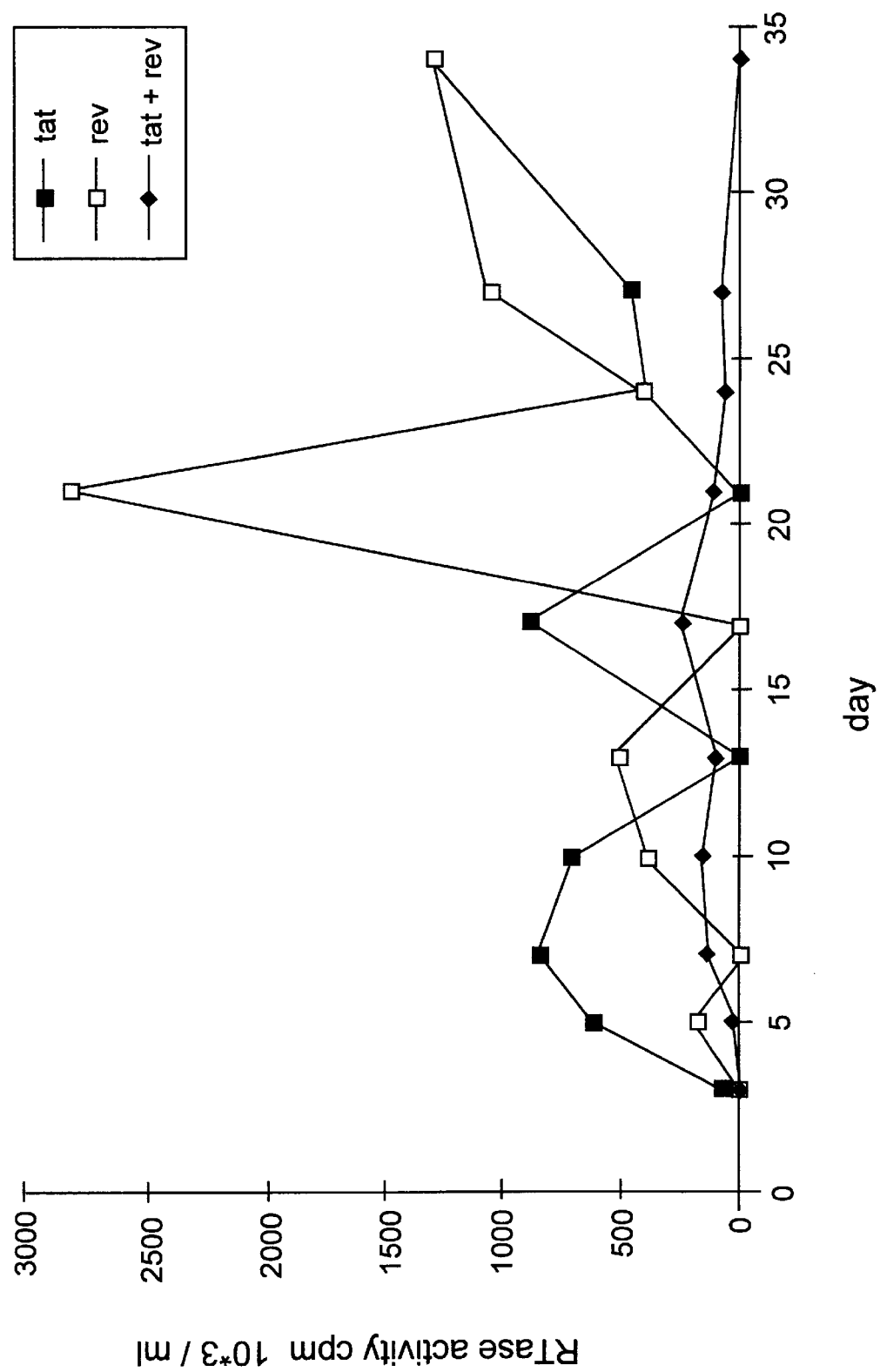
FIG. 3 shows the effects of the joint expression of the trans-dominant TAT and REV variants (♦) on the course of infection in cells infected with HIV, compared to the expression of a trans-dominant TAT variant (■) or that of a trans-dominant REV variant (□).

The results illustrated in FIG. 3 show that the reverse transcriptase activity of the CEM-A3 2350+2428 supernatants lies at a very low level during at least 35 days of culture. It should be noted that, in normal cells infected with HIV, reverse transcriptase activity is normally detected after 5 to 6 days as a result of the release of new viral particles into the medium, which goes on increasing rapidly with time until cell death ensues.

By way of comparison, the experiment is performed on CEM-A3 2350 and CEM-A3 2430 cell culture aliquots under strictly identical conditions. In this case, a delay is observed in the propagation of the virus, reflected in a reduced reverse transcriptase activity during the first 20 days of culture, but followed by an increase when culturing is continued.

EXAMPLE 3

Construction of Retroviral Vectors Coexpressing Trans-Dominant TAT and REV Variants and Establishment of Corresponding Amphotropic Lines A. Construction of the vector pTG4367

The vector M13TG2309 is subjected to a directed mutagenesis using the oligonucleotide OTG5254 reported in sequence identifier NO: 5, which enables the DNA sequence coding for the native REV protein to be modified at 5 points to create a trans-dominant REV variant (replacement of the codons coding for the residues $Gln^{74}$ by Gly, $Leu^{75}$ by Ser, $Leu^{78}$ by Glu, $Glu^{79}$ by Phe and $Leu^{81}$ by Asp). The vector M13TG4303 is obtained.

The retroviral vector pLXSP is digested with EcoRI-HpaI. An EcoRI-PstI fragment carrying the murine PGK promoter described in Adra et al. (1987, Gene, 60, 65–74) is isolated, the PstI site being blunt-ended by treatment with T4 polymerase. The vector thereby obtained undergoes deletion of the cassette for expressing the puromycin resistance gene. In order to do this, after digestion with ClaI-BamHI and treatment with the Klenow fragment of DNA polymerase, it is religated with itself so as to generate pTG2673.

Figure 4:
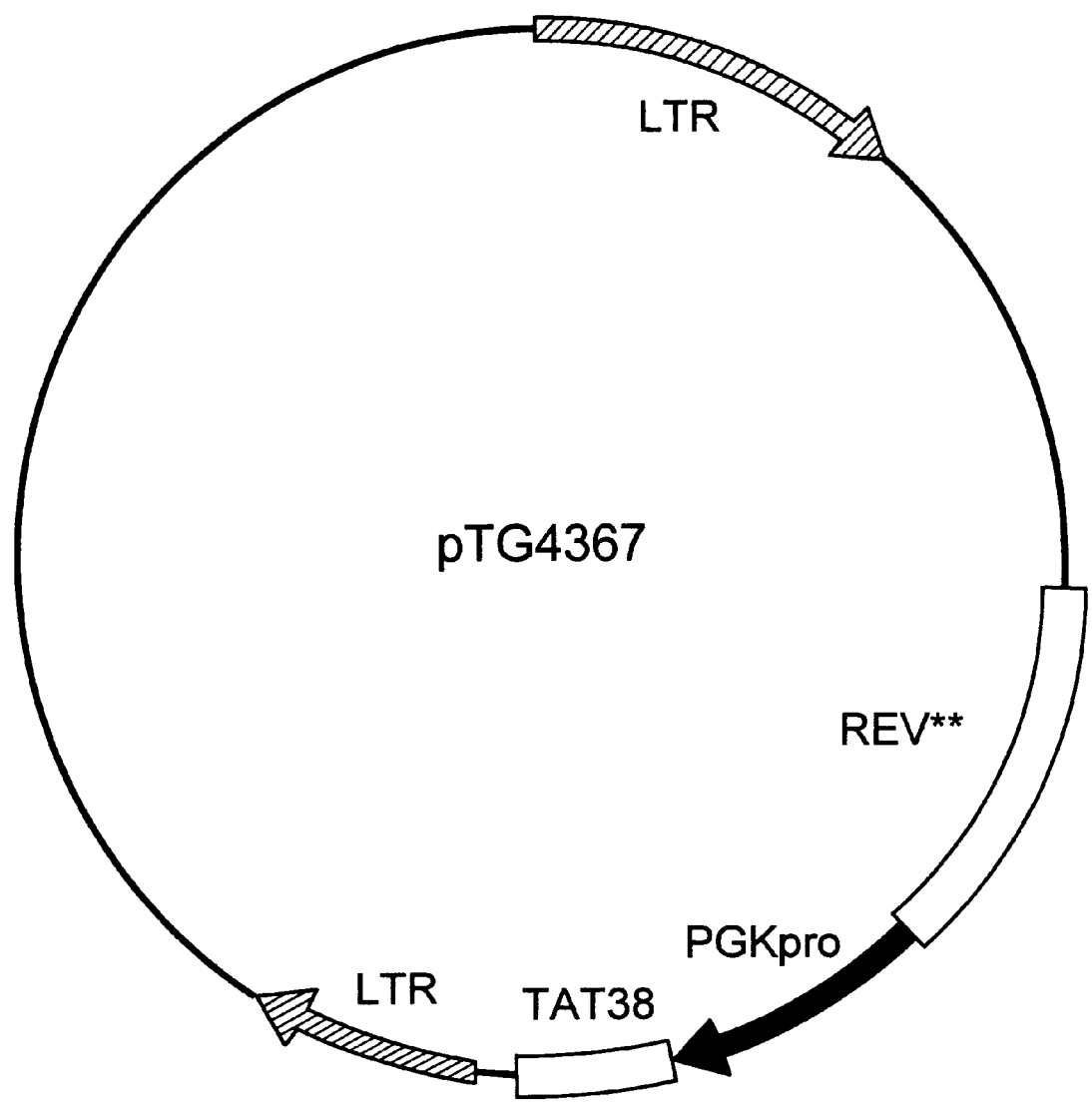
FIG. 4 shows diagrammatically the retroviral vector pTG4367 comprising the sequences coding for the trans-dominant variants TAT (Phe$^{38}$→Asp) and REV (Gln$^{74}$, Leu$^{75}$, Leu$^{78}$, Glu$^{79}$ and Leu$^{81}$→Gly, Ser, Glu, Phe and Asp) which is denoted hereinafter REV**, under the control of the murin PGK promoter (PGKpro) and the retroviral 5' LTR.

The BamHI fragment isolated from M13TG2316 is introduced into the vector pTG2673 previously digested with BamHI. The vector obtained is then digested with EcoRI and treated with the large Klenow fragment of DNA polymerase. In parallel, M13TG4303 is digested with BglII, treated with Klenow and then digested with PvuII. The fragment carrying the sequence coding for the 5-fold mutated trans-dominant REV variant is isolated and inserted into pTG2673 thus treated. pTG4367 (FIG. 4) is obtained, in which the DNA sequence coding for TAT ($Phe^{38}\rightarrow Asp$) is placed under the control of the PGK promoter, and that coding for trans-dominant REV under the control of the 5' LTR of the retroviral vector.

An amphotropic line is established from a cell line, termed encapsidation line, into which there is inserted an env gene of an amphotropic retrovirus, for example the PA317 line (Miller et al., 1986, Mol. Cell. Biol., 6, 2895–2902) or Gp. Env. Am. 12 (Markowitz et al., 1988, Virology 167, 400–406). The vector pTG4367 and any vector for selection, such as, for example, a vector containing the puromycin resistance gene under the control of the SV40 promoter, are transfected. The day following transfection, the cells are placed in a selective medium (6 μg/ml puromycin). The resistant cells producing amphotropic viral particles capable of infecting human cells are isolated.

A viral stock which could be used in gene therapy for infecting a patient's hematopoietic stem cells or lymphocytes can be built up.

B. Construction of the vector pTG8301 (expression of TAT ($Gin^{54}\rightarrow STOP$) fused with the product of the neo gene and of REV mutated at the level of residues 74, 75, 78, 79 and 81)

The construction of the trans-dominant TAT variant in which the glutamine (Gln) residue at position 54 of the native protein is replaced by a stop codon, is described in European Application EP 0,614,980. To summarize, the vector M13TG2306 (Example 1) is subjected to directed mutagenesis (Amersham kit) by means of the oligonucleotide OTG4376 (see SEQ ID NO: 3 of EP 0,614,980). M13TG2330 is obtained. In order to perform the fusion with the selectable gene, the latter is again subjected to a directed mutagenesis with the aim of destroying the STOP codon of the tat gene and of inserting therein an arm of three alanine residues corresponding to a NotI site. The mutagenic oligonucleotide OTG4413 (SEQ ID NO: 6) is used and M13TG2330* is generated.

In parallel, the neo selectable gene is amplified by PCR from the vector pAG60 (Colbere-Garapin et al., 1981, J.

Mol. Biol., 150, 1–4). In order to do this, conventional primers provided at their 5' ends with NotI sites are used. The PCR fragment thus obtained is cloned into NotI-linearized M13TG2330* to give M13TG6389. After digesting the latter with BamHI, the 1.2 kb fragment carrying the fusion gene encoding the hybrid product TAT followed by neo is purified. It is introduced into the BamHI site of the retroviral vector pTG2673 to give pTG6392.

Figure 5:
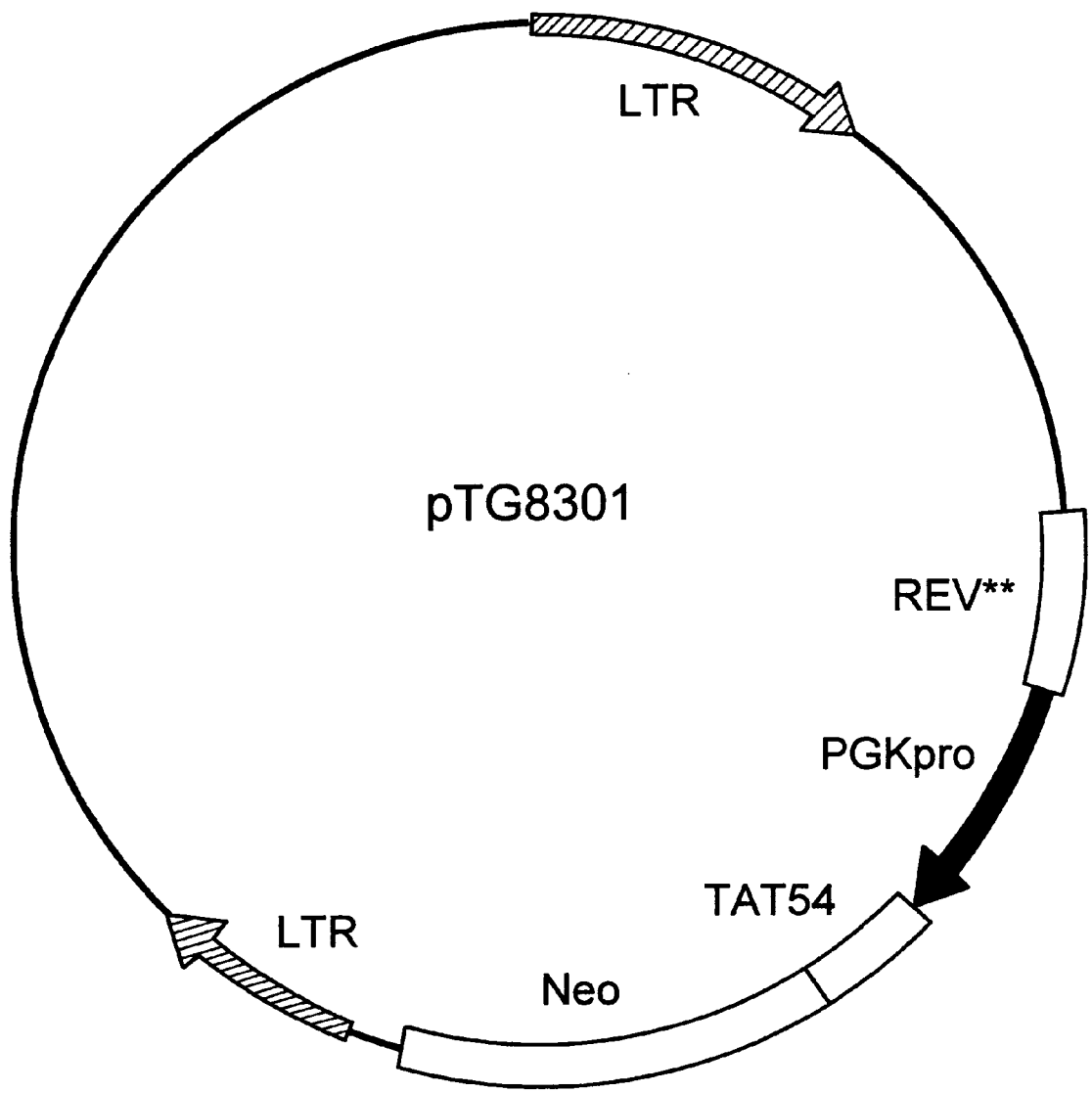
FIG. 5 illustrates the vector pTG8301 in which the sequences coding for the REV** mutant and for the fusion product TAT (Glns$^{54}$→STOP) (TAT54)—neo are placed under the control of the retroviral 5' LTR (LTR) and of the murin PGK promoter (PGK pro) respectively.

The vector M13TG4303 is subjected to directed mutagenesis in order to create a BglII site downstream of the stop codon of the trans-dominant REV, with the aim of facilitating the subsequent cloning steps. The oligonucleotide OTG 4370 (SEQ ID NO: 7) is used to this end. The BglII fragment (0.38 kb) thus generated is then finally inserted into the vector pTG6392. pTG8301 (FIG. 5) is obtained in which the gene encoding the transdominant REV mutant is placed under the control of the 5' LTR of the retroviral vector whereas the expression of the trans-dominant TAT variant fused with the product of the neo gene depends on the murine PGK promoter.

C. Construction of the vector pTG8313 (expression of TAT (Phe$^{38}$→Asp) fused with the product of the neo gene and of REV mutated at the level of residues 74, 75, 78, 79 and 81)

Figure 6:
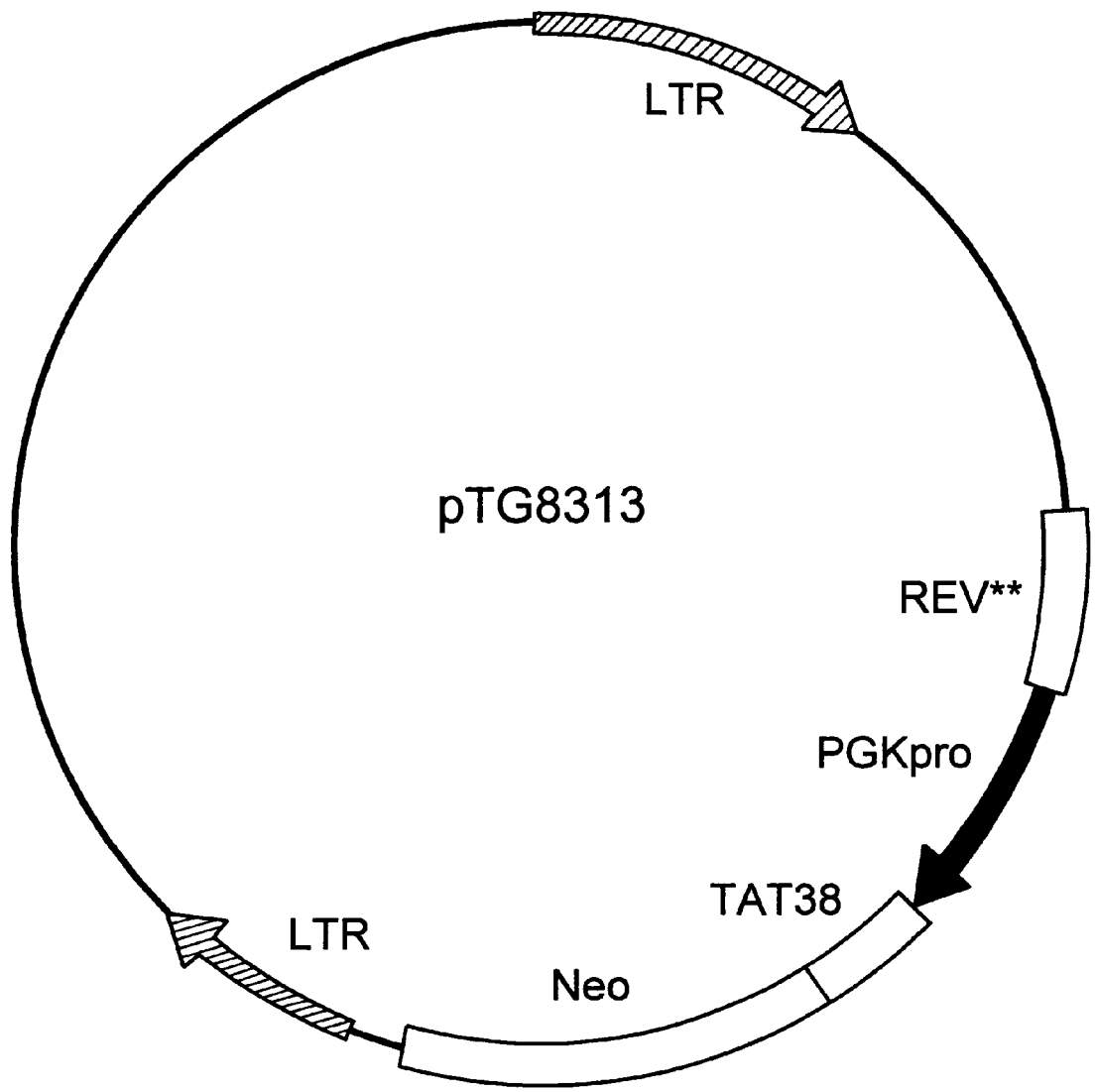
FIG. 6 illustrates the vector pTG8313 in which the sequences coding for the REV** mutant and for the fusion product TAT (Phe$^{38}$→Asp)—neo are placed under the control of the retroviral 5' LTR (LTR) and of the murin PGK promoter (PGK pro) respectively.

The vector M13TG6390 results from the insertion of the NotI fragment of M13TG6389 carrying the neo gene into M13TG2316. A NotI site was created beforehand in the latter upstream of the STOP codon of the TAT38 mutant by means of the mutagenic oligonucleotide OTG4413 described above. The BamHI fragment (1.2 kb) purified from M13TG6390 is then introduced into the vector pTG2673 previously digested with BamHI to give pTG8305. Finally, the 0.38 kb BglII fragment comprising the mutated rev gene is cloned into the EcoRI site (treated with Klenow) of the vector obtained at the preceding stage to generate pTG8313 (FIG. 6).

D. Construction of retroviral vectors pTG8315 and pTG8316

The 0.3 kb BamHI fragment derived from M13TG2316 (carrying TAT Phe$^{38}$→Asp) or from M13TG2330 (TAT (Glns$^{54}$→STOP) is inserted into the BamHI site of p polyIII-I* (Lathe et al., Gene, 1987, 57, 193–201), giving rise to p poly-2316 or p poly-2330. These are cleaved with EcoRI and PvuII and an EcoRI-NcoI fragment (whose sites are blunt-ended by treatment with Klenow) corresponding to the IRES elements of the EMCV virus (Eucephalomyocarditis Virus) is introduced. This fragment is derived from the vector IRES-βgeo described in international application WO 94/24301.

The neo gene is then cloned downstream of the IRES in the form of a blunt-ended fragment isolated from pAG60. Persons skilled in the art know how to generate a blunt-ended fragment from a prior art plasmid. It is introduced into the AccI site (treated with Klenow) of the previous construct. The vectors pTG6399 and pTG6398 comprising the bicistronic cassettes TAT (Phe$^{38}$→Asp)—IRES—neo and TAT (Gln$^{54}$→STOP)—IRES—neo, respectively, are obtained.

Figure 7:
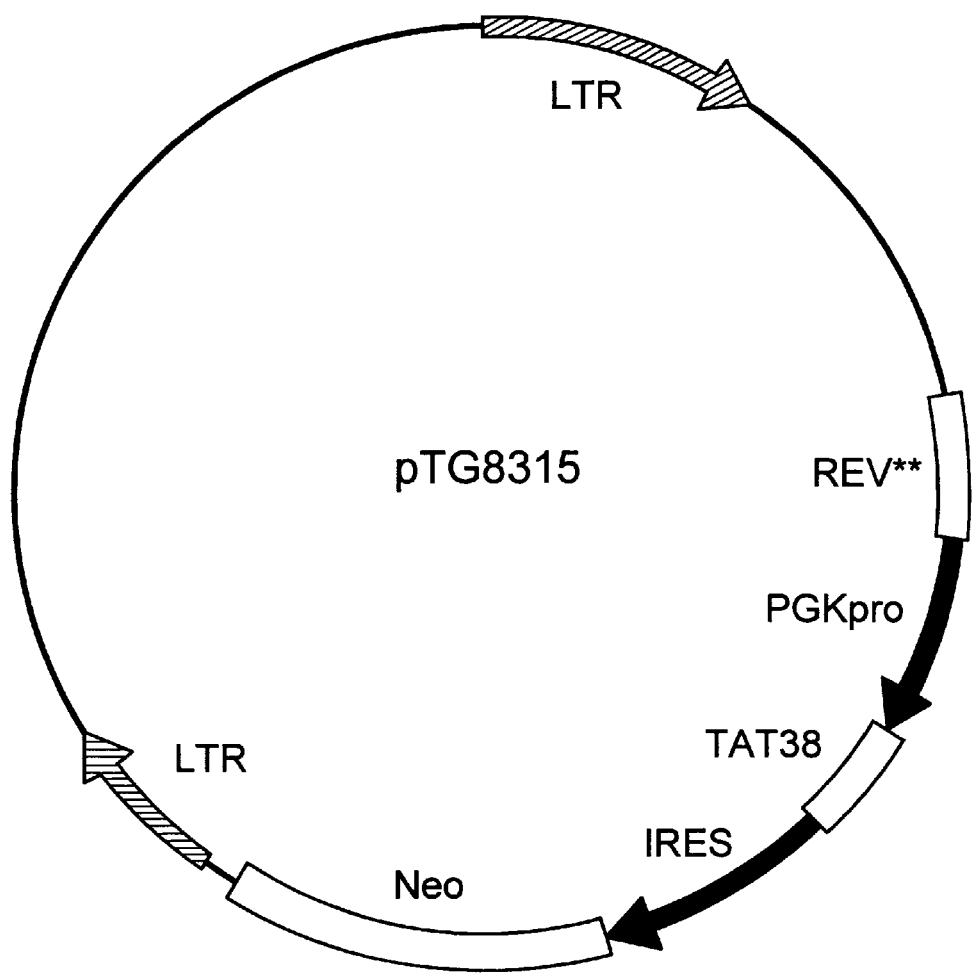
FIG. 7 illustrates the vector pTG8315 in which the sequences coding, on the one hand, for the REV** mutant and, on the other hand, for the products TAT38 and neo are placed under the control of retroviral 5' LTR (LTR) and of the murin PGK promoter (PGK pro) respectively.

In parallel, the BglII fragment (0.38 kb) purified from mutated M13TG4303 is treated with Klenow and then inserted into the vector pTG2673 digested with EcoRI and also treated with Klenow. The vector thus obtained is finally digested with XhoI so as to clone the XhoI fragment obtained from pTG6399 or from pTG6398. The vectors pTG8315 (FIG. 7) and pTG8316 are thus generated in which the modified rev gene (5 mutations) is under the control of the retroviral 5' LTR and the bicistronic cassette encoding TAT (Phe$^{38}$→Asp) or TAT (Gln$^{54}$→STOP) and the product of the neo gene is under the control of the PGK promoter.

E. Construction of the vectors inducible by the HIV native TAT protein

The BglII fragment (0.38 kb) carrying the trans-dominant rev gene is purified from mutated M13TG4303 and subcloned into the BamHI site of p polyIII-I*. The resulting vector is linearized with SmaI and the EcoRI°-NcoI° fragment carrying IRES is introduced therein. The neo gene in the form of a blunt-ended fragment described above is then inserted into the EcoRV site of the vector thus generated, so as to generate a bicistronic cassette containing the sequences encoding REV (Gln$^{74}$, Leu$^{75}$, Leu$^{78}$, Glu$^{79}$, Leu$^{81}$→Gly, Ser, Glu, Phe, Asp) and the product of the neo gene whose translation is reinitiated by the EMCV IRES.

This cassette is isolated by XhoI-XbaI digestion followed by treatment with Klenow and is inserted into the BalI site of the vector pTG4347. The latter results from the cloning into p polyIII-I* of a fragment containing the 3' part of the 5' LTR of HIV (Lai isolate), designated hereinafter "mini-LTR", and the SV40 virus polyadenylation signal. As a guide, the mini LTR corresponds to the ScaI-HindIII fragment of the HIV 5' LTR and has the elements ensuring transcription and transactivation by the native TAT protein. The vector thus generated is called pTG8314.

Figure 8:
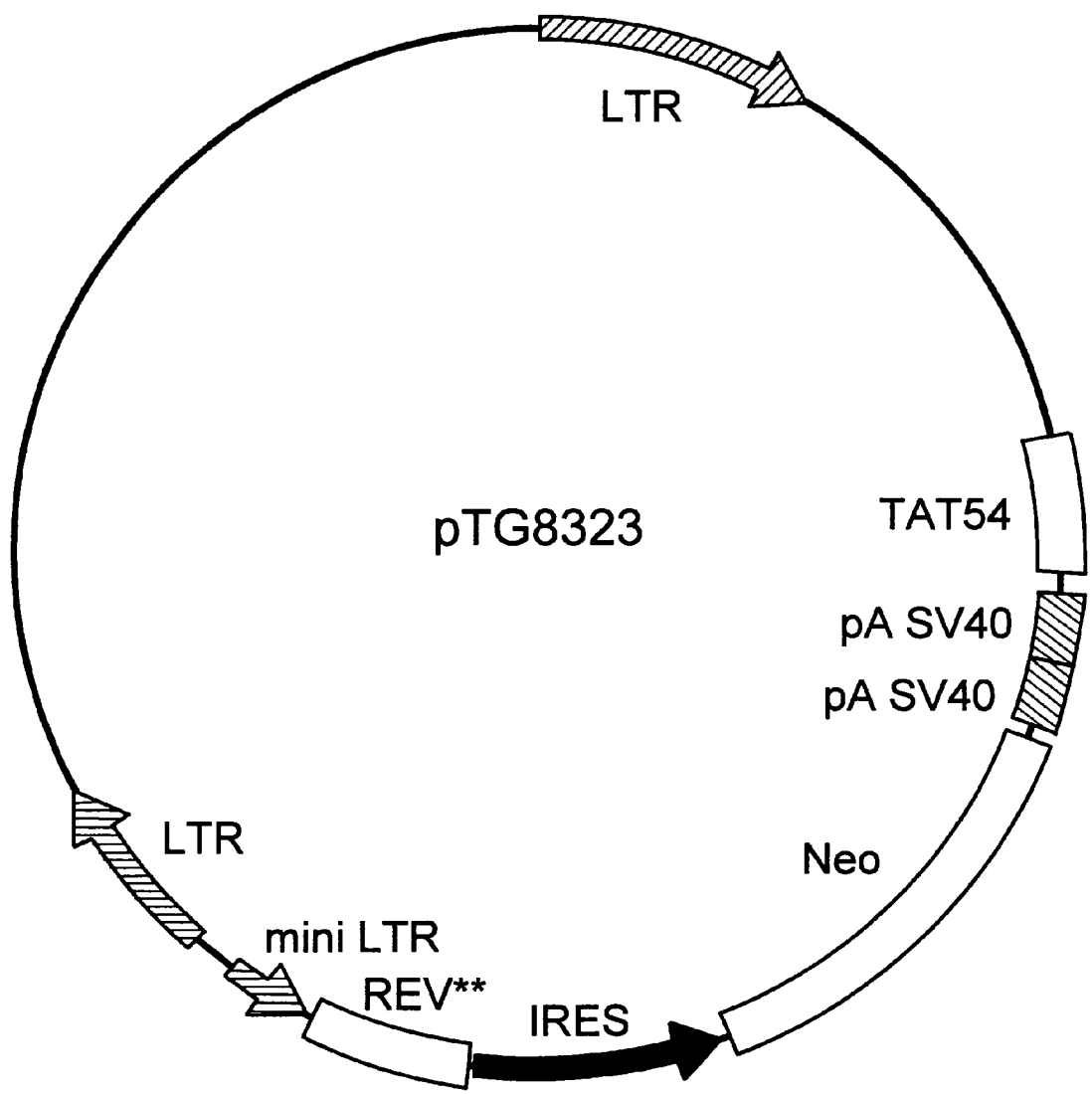
FIG. 8 illustrates the vector pTG8323 in which the sequences coding, on the one hand, for the REV** mutant and the Neo product and, on the other hand, for the TAT mutant (Gln$^{54}$→STOP) are placed under the control of the HIV mini LTR and of the retroviral 5' LTR respectively.

In parallel, the BamHI fragments of M13TG2316 and M13TG2330 comprising the sequences encoding the trans-dominant variants TAT (Phe$^{38}$→Asp) and TAT (Gln$^{54}$→STOP) respectively, are inserted into the vector pTG2682, which vector corresponds to pTG2673 lacking the PGK promoters. The NotI fragment isolated from pTG8314, treated with Klenow, is then finally introduced in the XhoI site (blunt-ended by treatment with Klenow) of both of the previous constructs derived from pTG2682. Vectors are obtained in which the respective trans-dominant tat genes are expressed constitutively under the control of retroviral 5' LTR, whereas the trans-dominant rev gene is expressed inducibly by the HIV native TAT protein under the control of the HIV mini LTR. Clones are preferably selected in which both expression cassettes are in the reverse orientation relative to each other (FIG. 8; pTG8323).

F. Evaluation of the functionality of the preceding constructs

The trans-dominant activity of the TAT and REV products produced by each of the constructs of Example 3 can be evaluated as above by transient cotransfection of human cells (for example of A549 ATCC CCL185 cells) with a reporter vector (TAT-dependent LTR-CAT or REV-dependent pTG1335) and a wild-type TAT or REV protein expression vector (pHMG-Tat or pHMG-Rev).

G. Constitution of infectious viral particles

Stocks of infectious viral particles comprising each of the constructs of Example 3 can be prepared in a conventional manner. Briefly, the retroviral vectors are transfected into the ecotropic encapsidation cells GP+E 86 (Markowitz et al., 1988, J. Virol., 62, 1120–1124). After selection of the neomycin-resistant cells, the culture supernatants are harvested in order to transduce an amphotropic encapsidation line, for example the PA317 line. The lines thus obtained will constitute the infectious viral particle-producing cells, which cells can be used in the context of an anti-AIDS gene therapy. Their capacity to induce resistance to HIV infection can be evaluated in vivo and in vitro as indicated in Example 2.

We claim:

1. A composition comprising at least:
(a) a first trans-dominant variant of the TAT protein of human immunodeficiency virus (HIV); said trans-dominant variant of the TAT protein having the sequence of SEQ ID NO: 1 which comprises at least one of the following modifications: (i) the phenylalanine residue at position +38 is replaced by an aspartic acid residue; (ii) the threonine residue at position +40 is replaced by an alanine residue; (iii) the lysine residue at position +41 is replaced by a glutamic acid residue; (iv) the isoleucine residue at position +45 is replaced by a serine residue; and (v) the tyrosine residue at position +47 is replaced by an arginine residue; and
(b) a second trans-dominant variant of the REV protein of HIV; said trans-dominant variant of the REV protein having the sequence of SEQ ID NO: 2 which comprises at least the following modifications: (i) the glutamine residue at position +74 is replaced by a glycine residue; and (ii) the leucine residue at position +75 is replaced by a serine residue;
wherein said composition inhibits viral replication.

2. The composition of claim 1, wherein the tramdominant variant of the REV protein has the sequence of SEQ ID NO: 2 wherein the glutamine residue at position +74 is replaced by a glycine residue, the leucine residue at position +75 is replaced by a serine residue, the leucine residue at position +78 is replaced by a glutamic acid residue the glutamic acid residue at position +79 is replaced by a phenylalanine residue and the leucine residue at position +81 is replaced by an aspartic acid residue.

3. A recombinant vector comprising:
(a) a first DNA sequence coding for a first trans-dominant variant of the TAT protein of HIV, placed under the control of the elements needed for its expression; said trans-dominant variant of the TAT protein having the sequence of SEQ ID NO: 1 which comprises at least one of the following modifications: (i) the phenylalanine residue at position +38 is replaced by an aspartic acid residue; (ii) the threonine residue at position +40 is replaced by an alanine residue; (iii) the lysine residue at position +41 is replaced by a glutamic acid residue; (iv) the isoleucine residue at position +45 is replaced by a serine residue; and (v) the tyrosine residue at position +47 is replaced by an arginine residue; and
(b) a second DNA sequence coding for a second trans-dominant variant of the REV protein of HIV, placed under the control of the elements needed for its expression; said trans-dominant variant of the REV protein having the sequence of SEQ ID NO: 2 which comprises at least the following modifications: (i) the glutamine residue at position +74 is replaced by a glycine residue; and (ii) the leucine residue at position +75 is replaced by a serine residue;

wherein said vector inhibits viral replication.

4. The recombinant vector of claim 3, wherein said vector is a virus selected from the group consisting of retroviruses, adenoviruses and adeno-associated viruses.

5. The composition of claim 1, which further comprises a pharmaceutically acceptable carrier.

6. The recombinant vector of claim 3, wherein said trans-dominant variant of the REV protein has the sequence of SEQ ID NO: 2 wherein the glutamine residue at position +74 is replaced by a glycine residue, the leucine residue at position +75 is replaced by a serine residue, the leucine residue at position +78 is replaced by a glutamic acid residue, the glutamic acid residue at position +79 is replaced by a phenylalanine residue and the leucine residue at position +81 is replaced by an aspartic acid residue.

7. A eukaryotic cell into the genome of which there are inserted:
  (a) a first DNA sequence coding for a first trans-dominant variant of the TAT protein of HIV, placed under the control of the elements needed for its expression; said trans-dormant variant of the TAT protein having the sequence of SEQ ID NO: 1 which comprises at least one of the following modifications: (i) the phenylalanine residue at position +38 is replaced by an aspartic acid residue; (ii) the threonine residue at position +40 is replaced by an alanine residue; (iii) the lysine residue at position +41 is replaced by a glutamic acid residue; (iv) the isoleucine residue at position +45 is replaced by a serine residue; and (v) the tyrosine residue at position +47 is replaced by an arginine residue; and
  (b) a second DNA sequence coding for a second trans-dominant variant of the REV protein of HIV, placed under the control of the elements needed for its expression; said trans-dominant variant of the REV protein having the sequence of SEQ ID NO: 2 which comprises at least the following modifications: (i) the glutamine residue at position +74 is replaced by a glycine residue; and (ii) the leucine residue at position +75 is replaced by a serine residue;
  wherein said cell inhibits viral replication.

8. The eukaryotic cell of claim 7, wherein said trans-dominant variant of the REV protein has the sequence of SEQ ID NO: 2 wherein the glutamine residue at position +74 is replaced by a glycine residue, the leucine residue at position +75 is replaced by a serine residue, the leucine residue at position +78 is replaced by a glutamic acid residue, the glutamic acid residue at position +79 is replaced by a phenylalanine residue and the leucine residue at position +81 is replaced by an aspartic acid residue.

9. A kit comprising:
  (a) a first trans-dominant variant of the TAT protein of human immunodeficiency virus (HIV); said trans-dominant variant of the TAT protein having the sequence of SEQ ID NO: 1 which comprises at least one of the following modifications: (i) the phenylalanine residue at position +38 is replaced by an aspartic acid residue; (ii) the threonine residue at position +40 is replaced by an alanine residue; (iii) the lysine residue at position +41 is replaced by a glutamic acid residue; (iv) the isoleucine residue at position +45 is replaced by a serine residue; and (v) the tyrosine residue at position +47 is replaced by an arginine residue; and
  (b) a second trans-dominant variant of the REV protein of HIV; said trans-dominant variant of the REV protein having the sequence of SEQ ID NO: 2 which comprises at least the following modifications: (i) the glutamine residue at position +74 is replaced by a glycine residue; and (ii) the leucine residue at position +75 is replaced by a serine residue;
  wherein the combination of said first and second trans-dominant variant inhibits viral replication.

10. The kit of claim 9, wherein said trans-dominant variant of the REV protein has the sequence of SEQ ID NO: 2, wherein the glutamine residue at position +74 is replaced by a glycine residue, the leucine residue at position +75 is replaced by a serine residue, the leucine residue at position +78 is replaced by a glutamic acid residue, the glutamic acid residue at position +79 is replaced by a phenylalanine residue and the leucine residue at position +81 is replaced by an aspartic acid residue.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 86 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Human immunodeficiency virus type 1
        (B) STRAIN: Lai
        (C) INDIVIDUAL ISOLATE: sequence of the TAT protein of HIV-1

(xi) SEQUENCE DESCRIPTION: SEQ ID NO:1:

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

(2) INFORMATION FOR SEQ ID NO:2:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Human immunodeficiency virus type 1
        (B) STRAIN: Lai
        (C) INDIVIDUAL ISOLATE: sequence of the rev protein of the
            HIV-1 virus (xi) SEQUENCE DESCRIPTION: SEQ ID NO:2:

Met Ala Gly Arg Ser Gly Asp Ser Asp Glu Asp Leu Leu Lys Ala Val
1               5                   10                  15

Arg Leu Ile Lys Phe Leu Tyr Ala Ser Asn Pro Pro Asn Pro Glu
            20                  25                  30

Gly Thr Arg Gln Ala Arg Arg Asn Arg Arg Arg Trp Arg Glu Arg
            35                  40                  45

Gln Arg Gln Ile His Ser Ile Ser Glu Arg Ile Leu Ser Thr Tyr Leu

```
                    50                  55                  60
Gly Arg Ser Ala Glu Pro Val Pro Leu Gln Leu Pro Pro Leu Glu Arg
 65                  70                  75                  80

Leu Thr Leu Asp Cys Asn Glu Asp Cys Gly Thr Ser Gly Thr Gln Gly
                 85                  90                  95

Val Gly Ser Pro Gln Ile Leu Val Glu Ser Pro Thr Val Leu Glu Ser
            100                 105                 110

Gly Thr Lys Glu
            115
```

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: mutagenesis oligonucleotide (TAT
            Phe38 to Asp)

(xi) SEQUENCE DESCRIPTION: SEQ ID NO:3:

TAAAGCTTTT GTTGTGTCAC AAACTT                                      26

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: mutagenesis oligonucleotide (REV
            Gln, Leu to Gly, Ser)

(xi) SEQUENCE DESCRIPTION: SEQ ID NO:4:

TCTCTCAAGC GGTGGGGATC CAAGAGGCAC AGG                            33

(2) INFORMATION FOR SEQ ID NO:5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: mutagenesis oligonucleotide (xi) SEQUENCE DESCRIPTION: SEQ ID NO:5:

-continued

```
ATCAAGAGTA TCTCTGAATT CCGGTGGGGA TCCAAGAGGC A                41
```

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: synthetic oligonucleotide (OTG4413)

(xi) SEQUENCE DESCRIPTION: SEQ ID NO:6:

```
TCTCTCCACC TTCGCGGCCG CTTCCTTCGG GCCT                         34
```

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: synthetic oligonucleotide (OTG4370)

(xi) SEQUENCE DESCRIPTION: SEQ ID NO:7:

```
GGCATTGAGA GATCTAACAG CA                                     22
```